United States Patent [19]

Daoud et al.

[11] Patent Number: 4,944,485
[45] Date of Patent: Jul. 31, 1990

[54] CLAMP FOR FLEXIBLE TUBING

[75] Inventors: Adib G. Daoud; Fred W. Bacher, both of San Diego, Calif.

[73] Assignee: IVAC Corporation, San Diego, Calif.

[21] Appl. No.: 398,887

[22] Filed: Aug. 28, 1989

[51] Int. Cl.⁵ ............................................. F16K 7/02
[52] U.S. Cl. ...................................... 251/9; 251/369; 137/560
[58] Field of Search .................... 251/4, 9, 10, 369; 137/560, 343

[56] References Cited

U.S. PATENT DOCUMENTS

| | | | |
|---|---|---|---|
| 820,216 | 5/1906 | Leffingwell et al. | |
| 1,968,454 | 7/1934 | Hyatt | 251/5 |
| 2,806,482 | 9/1957 | Norris et al. | 251/9 X |
| 2,832,560 | 2/1957 | Grigsby | 251/9 |
| 3,539,081 | 11/1970 | Norton et al. | 251/9 X |
| 3,698,681 | 10/1972 | Lacey | 251/10 |
| 3,942,228 | 3/1976 | Buckman et al. | 24/255 |
| 4,091,815 | 5/1978 | Larsen | 128/325 |
| 4,193,174 | 3/1980 | Stephens | 24/249 |
| 4,247,076 | 1/1981 | Larkin | 251/7 |
| 4,460,358 | 7/1981 | Somerville et al. | 604/250 |
| 4,689,043 | 8/1987 | Bisha | 604/250 |

Primary Examiner—John C. Fox
Attorney, Agent, or Firm—Fulwider, Patton, Lee & Utecht

[57] ABSTRACT

The clamp for flexible tubing may be used in conjunction with an infusion pump instrument or separately. The clamp includes a pair of elongated clamping members pivotally hinged together and biased to clamp a segment of flexible tubing received between the clamping members. A latch is also preferably provided for allowing the clamping members to be releasably latched apart. The latch, and the elongated clamping members are arranged in a manner such that when the clamp has a segment of flexible tubing received between the clamping members and the clamp and tubing are set between the housing and door of an infusion pump, closing the door causes the clamp to release to an open position allowing fluid flow, and opening the door causes the clamp to automatically move to a closed position, clamping the tubing so as to prevent fluid flow.

7 Claims, 3 Drawing Sheets

CLAMP FOR FLEXIBLE TUBING

BACKGROUND OF THE INVENTION

1. Field of the Invention:

This invention relates generally to a clamp for flexible tubing, and more particularly relates to a clamp for use with an instrument to be used with the tubing, to automatically pinch off the tubing to prevent fluid flow when the tubing is removed from the instrument and to permit fluid flow when the clamp and tubing are received in the instrument The clamp is particularly adapted for use with an intravenuous infusion pump.

2. Description of Related Art:

Tube clamping arrangements generally provide a squeezing action to restrict fluid flow in the tubing. Various types of clamps are known having lever arms pivotally connected at one end, and frequently having means for locking the lever arms into engagement clamping the tubing closed. Roller clamps and slidable clamps which may be locked into position are also known. Generally such tubing clamps need to be manually set, although they may have a spring arrangement for biasing the clamps in an open position.

In intravenous infusion pumps which operate to force parenteral fluids through intravenous tubing, additional control of fluid flow is generally achieved by use of a conventional tubing clamp outside of the infusion pump. The clamp must be set in the correct position by an operator before starting or stopping the infusion pump. Clamping mechanisms built into infusion pumps are also known which involve separate tube pinching and latching mechanisms. However, it would be desirable to provide a clamping mechanism which need not be formed as part of the complex mechanism of an infusion pump, which would cooperate with the mode of operation of the infusion pump on the flexible tubing, and which could also be manually opened and closed separately and apart from the operation of the infusion pump, to allow the tubing and clamp arrangement to be used either with the infusion pump, or with a gravity control type IV administration system. It is desirable to provide such a clamp with an automatic clamping function so that fluid would only normally be permitted to flow through the tubing when the clamp is associated with the infusion pump. It would also be desirable to permit manual control with the clamping operations so that the clamp could be latched in an open position, for instance, to allow fluid flow which could be regulated by other means, such as by a conventional roller clamp. The present invention addresses these needs.

SUMMARY OF THE INVENTION

The present invention provides a clamp for flexible tubing which may be used in conjunction with an infusion pump instrument, or separately. The clamp includes a pair of elongated clamping members pivotally hinged together and biased to clamp a segment of flexible tubing received between the clamping members. A latch is also preferably provided for allowing the clamping members to be releasably latched apart. The latch, and the elongated clamping members are arranged in a manner such that when the clamp has a segment of flexible tubing received between the clamping members and the clamp and tubing are set between the housing and door of an infusion pump, closing the door causes the clamp to release to an open position allowing fluid flow. Opening the door causes the clamp to automatically move to a closed position, clamping the tubing so as to prevent fluid flow.

Briefly, and in general terms, a clamp for flexible tubing comprises first and second elongated clamping members pivotally hinged together and having gripping means for restricting fluid flow in the tubing; means for biasing the gripping means together to clamp the flexible tubing received in the clamp to prevent fluid flow; and means for releasably latching the gripping means apart to allow fluid flow through the segment of tubing.

In a preferred embodiment, the first and second clamping members are pivotally hinged together intermediate the ends of the clamping members, and the latch and clamping members are adapted so as to allow fluid flow through the tubing when the clamp and tubing are received in a space between door and housing of a pump mechansim with the door in a closed position, and to prevent fluid flow through the tubing when the clamp and tubing are released from between the pump door and housing.

Other aspects and advantages of the invention will become apparent from the following detailed description and the accompanying drawings, illustrating by way of example the features of the invention.

DETAILED DESCRIPTION OF THE INVENTION

Figure 1:
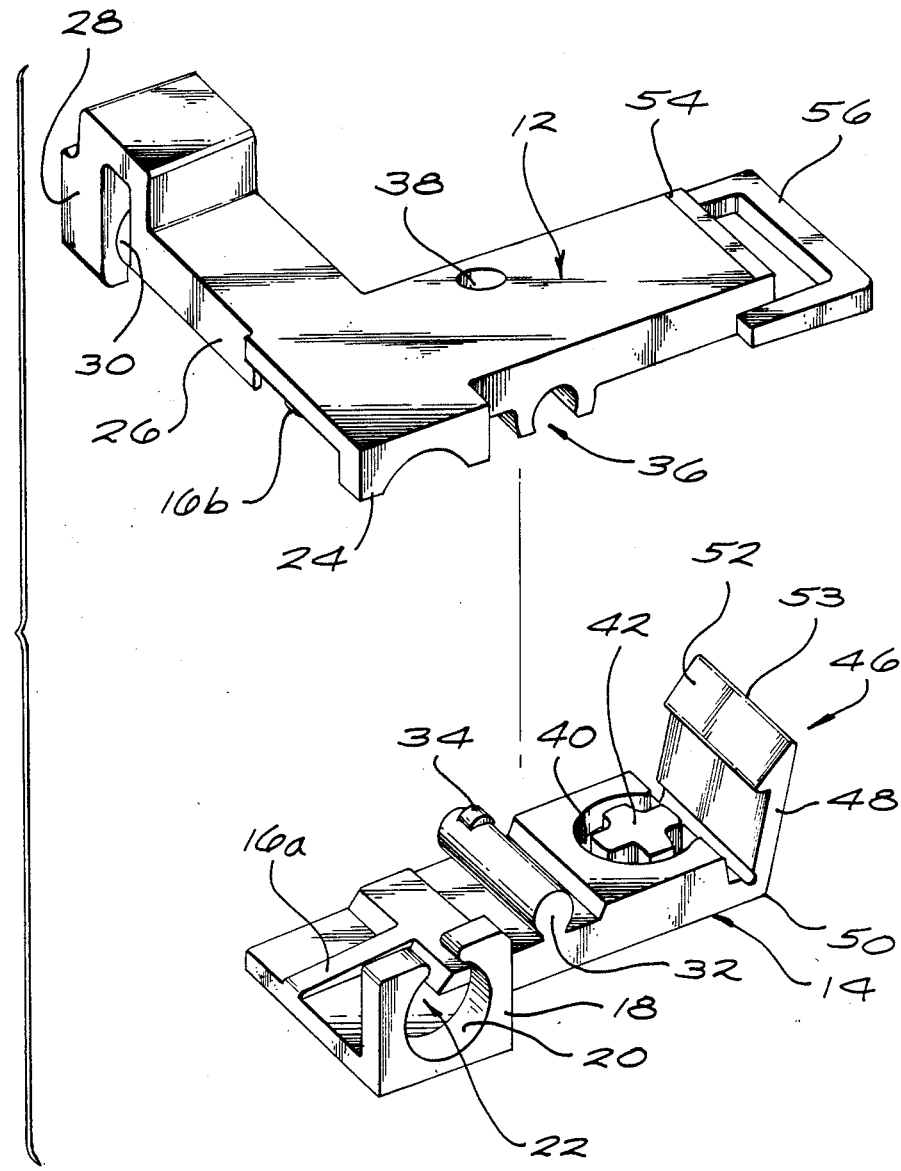
FIG. 1 is an exploded perspective view of the clamp of the invention.
Figure 2:
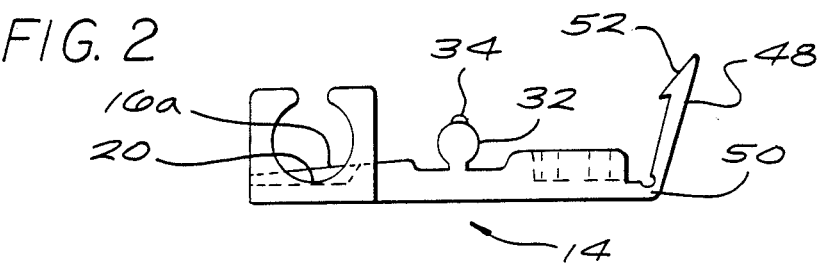
FIG. 2 is a side elevational view of one elongated clamping member including a latch arm.
Figure 3:
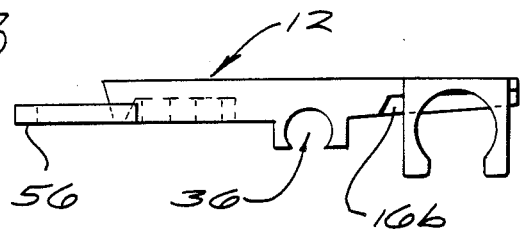
FIG. 3 is a side elevational view of the other elongated clamping member which includes a tubing guide extension.
Figure 4:
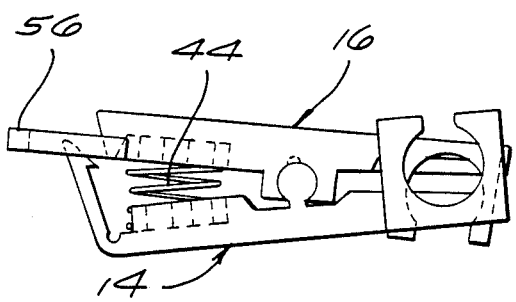
FIG. 4 is a side elevational view of the assembled clamp in an unlatched position biased to clamp a tubing segment and prevent fluid flow.
Figure 5:
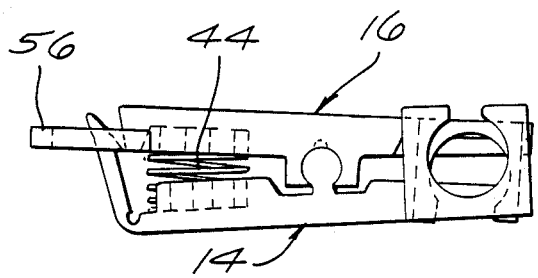
FIG. 5 is a side elevational view of the assembled tube clamp in an open position which would occur when the clamp is placed between the door and housing of a pump having a maximum door gap.
Figure 6:
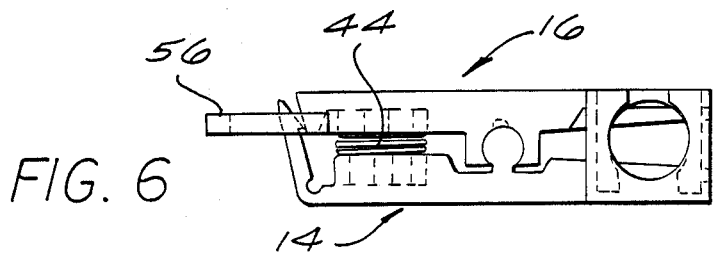
FIG. 6 is a side elevational view of the assembled tube clamp in an opened position as it would appear when the tube clamp is received between the door and housing of a pump with a minimum door gap.
Figure 7:
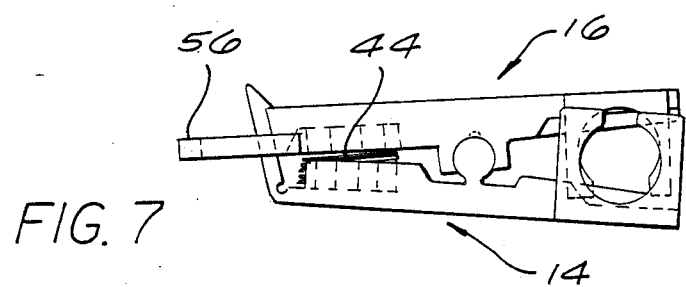
FIG. 7 is a side elevational view of the assembled tube clamp latched in an open position.

As is shown in the drawings for purposes of illustration, the invention is embodied in a clamp for flexible tubing in an intravenous administration set. The clamp and tubing may be received between the door and inner housing wall of an infusion pump to automatically cooperate with the infusion pump. No modification of the pump mechanism is required, and the clamp can also be used in cooperation with the pump, or separately, as the clamp can be manually latched or unlatched. The clamp automatically pinches off the tubing when the IV set is removed from the pump, but a nurse can override this automatic pinching action so that the IV flow may be regulated by other means, such as by a roller clamp. The clamp automatically resets to allow fluid flow through the tubing when the clamp is installed in the pump mechanism between the housing and the closed door of the pump.

In accordance with the invention, there is therefore provided a clamp for flexible tubing, comprising means for receiving the flexible tubing, including first and second elongated clamping members, pivotally hinged together and having gripping means for restricting fluid flow within said tubing; means for biasing the gripping means together to clamp the flexible tubing received therebetween; and means for releasably latching the gripping means apart.

The invention also provides for a clamp for flexible tubing for use in a pump having a housing and a door having an open and a closed position, the pump being adapted to receive the tubing and the clamp in a space formed between the housing and the door when the door is in the closed position, the clamp comprising: means for receiving the flexible tubing including first and second elongated clamping members each having first and second ends and means for gripping said tubing, one of the clamping members having a pivot hinge member intermediate the first and second ends of the member, and the other clamping member having a corresponding socket for receiving the pivot hinge member intermediate the first and second ends of the other member; means for biasing the gripping means together to clamp the flexible tubing received therebetween; and latching means for releasably latching the gripping means apart in an engaged position, the gripping means normally being free to move to clamp the flexible tubing when said latching means is in a disengaged position responsive to the means for biasing when the clamp is not received in the space between the pump housing and the door; and the latching means being forced to an intermediate disengaged position when the clamp is received in the space between the housing and the door in the pump door closed position, whereby the tubing received in the pump and the clamp is unclamped when the door is in the closed position.

As is shown in the drawings, a clamp 10 according to the invention includes a first clamping member 12, shown as the upper member in FIG. 1, and a second clamping member 14, or base, shown as the lower clamping member in FIG. 1. Each of the clamping members have substantially flat outside surfaces. At one end of each of the clamping members there are slanted ribs, 16a, b, for gripping the tubing when the tubing is placed between the ribs, each of the ribs decreasing in height as they extend toward the edge of each clamping member. When the outside surfaces of the elongated clamping members are parallel to each other, as occurs when the clamp is locked between the door and housing wall of an infusion pump, these ribs are sufficiently spaced apart to allow fluid flow through flexible tubing received between the ribs.

A guide member 18 is formed on the lower clamping member adjacent to the lower rib portion, for retaining the flexible tubing in place over the lower rib, and includes an aperture 20 formed in the guide, and a slot 22 in the guide aperture to allow flexible tubing to be pressed into the aperture. A partial upper guide member 24 is formed in the upper clamping member near the upper rib 16b, to be opposite the lower guide member and to cooperate with the lower guide member in retaining the flexible tubing in place between the ribs of the jaws of the clamping members.

The upper and lower clamping members of the clamp are preferably formed of plastic which is injection molded in the form desired. The upper and lower clamping members can be formed with a very thin web of plastic attaching the two pieces together, so that the complete clamp can be molded together as one piece. A guide extension 26 is preferably made of a similar plastic, and is preferably solvent bonded to the upper clamping member opposite the upper partial guide and adjacent to the upper rib of the jaw, and further includes an upper slotted tubing guide 28 at the distal end of the extension, having an aperture 30 for receiving the flexible tubing in a manner similar to that of the lower slotted tubing guide. Alternatively, the upper extension guide and upper slotted guide can be formed as a part of the upper clamping member in the injection molding process, if desired.

The lower clamping member includes a pivot hinge member 32 comprising a rounded head portion and neck portion generally centrally located on the lower clamping member extending transversely across the inside surface of the lower clamping member. The upper clamping member includes a socket 36 for receiving the pivot hinge member. The hinge member may optionally include a detent bump 34, and the upper clamping member may also include a corresponding detent socket or hole 38 for receiving the detent bump. The pivot hinge member and socket are formed in opposing relationship on the inner facing sides of the clamping members and are designed to be a snap fit. Of course, the positions of the pivot hinge member and socket could reversed, so that the pivot hinge member could be placed on the upper clamping member and the socket and detent socket could be placed on the lower clamping member.

In the lower clamping member, on the other side of the pivot hinge opposite the rib, a spring recess 40 is formed along with a center post 42, for receiving and retaining a coil compression spring 44, which biases the jaws of the clamping members together. The compression spring is preferably also insert molded into the upper clamping member. Alternatively, the spring socket may be formed in the upper clamping member with the compression spring being insert molded into the lower half of the clamp. When the assembled clamp is placed between the inner wall of a door of an infusion pump and an inner housing wall of the infusion pump, in which there is a space or door gap when the door is closed, such that the wall of the closed door and the adjacent wall of the housing are substantially parallel, tubing placed between the ribs of the clamping members will not be pinched off, allowing fluid to flow through the tubing.

A typical flexible IV tubing has a diameter when fully occluded of approximately 0.055 inches. The clamping members are to be formed with corresponding dimensions so that the tubing is pinched off between the ribs when the ribs are generally parallel, with a spacing between the ribs of approximately 0.055 inches. The compression spring provides sufficient biasing force to pinch off the tubing between the ribs of the clamp, and in the normally unlatched position of the clamp. The outer surfaces of the clamping members are flat, and are designed to be parallel when the ribs are in an open position, spaced apart sufficiently so that when flexible tubing is received between the ribs, fluid flow through the tubing is permitted. Thus, when the clamp and tubing are placed within the door gap between the inner wall of the door and the inner housing wall of an infusion pump, and the door is closed, the outside surfaces of the elongated clamping members are forced to be parallel to each other, allowing fluid flow through the flexible tubing. However, as soon as the door is opened, the clamping members are released to return their normal position, and the compression spring biases the ribs to close upon the flexible tubing, occluding fluid flow.

Another significant feature of the invention is the latch 46, having a latch arm 48 which extends from the end of the lower clamping member opposite the lower rib, and preferably adjacent to the compression spring, the latch arm pivoting at the living hinge 50. The latch includes a latch flange 52 which cooperates to latch upon a friction surface 54 formed on the upper surface of the corresponding end of the upper clamping member. The extreme end of the latch arm comprises a corner 53 of the latch flange extending beyond the upper surface of the upper clamping member when the latch is engaged. When the clamp is latched, with the corner extending beyond the friction surface, the ribs are latched in an open position, allowing fluid flow through fluid tubing received therebetween. When the tubing and clamp are received between the door and housing of an occlusion pump and the door is closed, the latch flange will be forced to disengage from the latch friction surface, releasing the clamp to the unlatched condition in which the jaws of the clamp are held open, allowing fluid flow to continue through the tubing. In the preferred embodiment, the distal end of the upper clamping member opposite the upper rib also includes a latch keeper 56 reaching around the latch 46, but providing sufficient space for latching and unlatching of the clamping members while retaining the latch in a position in which it can be readily placed in a latched or unlatched condition manually by an operator. The opening and closing of the tubing clamp is further illustrated in FIGS. 4–7.

Figure 8:
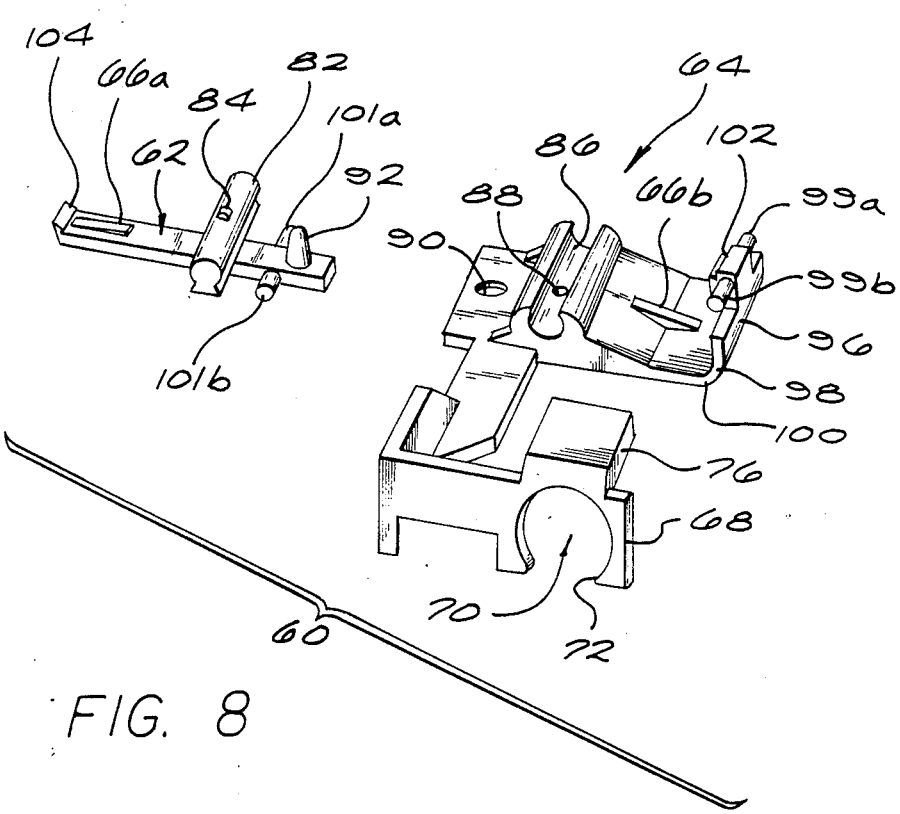
FIG. 8 is an exploded perspective view of an alternative embodiment of the tube clamp.

An alternative embodiment of the clamp of the invention is illustrated in FIG. 8. The clamp 60 includes the first or upper clamping member 62 shown joined to the second or lower clamping member 14, or base member, by a thin web of plastic formed during the injection molding process. An upper rib 66a is formed in the upper clamping member to cooperate with and oppose the rib 66b on the base of the clamp. The ribs are formed to open outwardly as they extend toward the adjacent end of the clamping members when the clamping members are joined together. A guide 68 is formed with an aperture 70 and a slot 72 for receiving flexible tubing, and is connected to the lower clamping member by the extension 76, which may be either formed along with the lower clamping member in the injection molding process, or solvent bonded to the lower clamping member, the extension piece and lower clamping member typically being formed of the same type of plastic material.

In the alternative embodiment, the upper clamping member includes the pivot hinge member 82 having the rounded head and neck portion connecting the pivot hinge member to the upper clamping member, the pivot hinge member extending transversely of the elongated upper clamping member. A detent bump 84 is also centrally located on the pivot hinge member, in such a fashion so that as the pivot hinge member is received in the opposing socket 86 on the base member, the detent bump is received in a slot 88, to prevent the pivot hinge member from moving transversely within the hinge socket.

A spring recess 90 is formed in the base clamping member at the end opposite from the lower rib, while a center post 92 is formed opposite to the spring recess in the upper clamping member for retaining a compression spring in place.

A latch 96 is formed in the base member adjacent to the lower rib, with a latch arm 98 extending from the living hinge portion 100 up to gripping posts 99a,b, which may be pressed inwardly towards the pivot hinge member at the same time similar gripping posts 101a,b formed on the upper clamping member adjacent to the spring center post are pressed against the compression force of the spring, to open the jaws of the clamp and latch the clamp in an open position. The latch flange surface 102 presses against the corresponding end surface 104 of the upper clamping member adjacent the upper rib. The clamp can be manually released to its normally closed position by an operator pulling the gripping posts 99a, 99b outwardly to allow the compression spring to close the jaws and occlude fluid flow through the tubing.

It will be appreciated that various alternatives in the structure of the invention can be employed to create a clamping device which will operate in similar fashion as that of the invention. For example, a torsion spring or leaf spring could be employed at the pivot hinge member to replace the compression spring, in order to bias the ribs of the clamping members together to close the jaws of the clamp upon the flexible tubing. Other guide structures and extension members may also be suitable, such as guide members having an aperture with a slot opening transversely, and in an plane parallel to that of the longitudinal clamping members rather than perpendicular to the clamping members as is illustrated.

In view of the foregoing, it has been demonstrated that the clamp for a flexible tubing is especially suitable for use in conjunction with an infusion pump apparatus. The clamp can operate in conjunction with, or independently of the pump instrument, requiring no modification of existing infusion pump systems.

Although specific embodiments of the invention have been described and illustrated, it is clear that it is susceptible to numerous modifications and adaptations within the ability of those skilled in the art and without the exercise of the inventive faculty. Thus, it should be understood that various changes in form detail and use of the present invention may be made without departing from the spirit and scope of the invention.

We claim:

1. A clamp for flexible tubing for use in a means for delivering fluid having a housing and a door mounted on said housing to be adjacent said housing in a closed position, said means for delivering fluid being adapted to retain said tubing and said clamp in a space between said housing and said door in the closed position, said clamp comprising:

means for receiving said flexible tubing, including first and second elongated clamping members each having first and second ends, each clamping member having gripping means adjacent one of said ends for restricting fluid flow in said tubing when said tubing is clamped therebetween, one of said clamping members having a pivot hinge member intermediate said one clamping member first and second ends, and the other clamping member having a corresponding socket for receiving said pivot hinge member intermediate said other clamping member first and second ends;

means for biasing said gripping means together to clamp said flexible tubing received therebetween; and latch means for releasably latching said gripping means apart in an engaged position, said clamping members being otherwise free to move to a disengaged position clamping said flexible tubing responsive to said means for biasing when said clamping members are not latched apart, and said latching means being forced to an intermediate disengaged position when said clamp is received in said space between said housing and said door, and said door is in the closed position, whereby said tubing received in said means for receiving fluid and said clamp is unclamped when said door is in the closed position, and said tubing becomes clamped when said door is moved to an open position.

2. The clamp of claim 1, wherein at least one of said first and second elongated clamping members includes a guide member for receiving and retaining the flexible tubing within said means for receiving the flexible tubing.

3. The clamp of claim 2, wherein one of said clamping members includes a guide member connected to said clamping member by an extension means.

4. The clamp of claim 1, wherein said means for biasing said clamping members together comprises a compression spring, and one of said clamping members include a spring well for receiving and retaining at least a portion of said spring.

5. The clamp of claim 1, wherein each of said gripping means comprises a rib member extending substantially from a location at which the clamping members are pivotally hinged together toward the adjacent distal end of the clamping member, each rib having a height dimension which decreases as each said rib extends toward said adjacent distal end.

6. The clamp of claim 1, wherein said means for releasably latching said clamping members apart includes a latch arm connected to one of said clamping members by means of a living hinge.

7. The clamp of claim 6, wherein one of the clamping members includes a latch keeper means for retaining said latch arm adjacent to the end of the clamping member bearing said latch keeper.

* * * * *

UNITED STATES PATENT AND TRADEMARK OFFICE
CERTIFICATE OF CORRECTION

PATENT NO. : 4,944,485

DATED : July 31, 1990

INVENTOR(S) : Adib G. Daoud; Fred W. Bacher

It is certified that error appears in the above-identified patent and that said Letters Patent is hereby corrected as shown below:

Column 5, line 40, delete "shown" and insert after the words "member 62"  -- which can be --

Column 5, line 41, delete "14" and insert after the words "clamping member"  -- 64 --

Signed and Sealed this

Sixth Day of April, 1993

*Attest:*

STEPHEN G. KUNIN

*Attesting Officer*          Acting Commissioner of Patents and Trademarks